United States Patent
Liao et al.

(10) Patent No.: US 12,036,300 B2
(45) Date of Patent: **\*Jul. 16, 2024**

(54) METHODS AND COMPOSITIONS FOR IMPROVING SKIN

(71) Applicant: L'OREAL, Paris (FR)

(72) Inventors: I-Chien Liao, Princeton, NJ (US); Patricia Brieva, Manalapan, NJ (US); Franck Juchaux, Aulnay-sous-Bois (FR); Charbel Bouez, Hoboken, NJ (US); Qian Zheng, Bridgewater, NJ (US); Kun Qian, Millburn, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/218,773

(22) Filed: Mar. 31, 2021

(65) Prior Publication Data

US 2022/0313578 A1    Oct. 6, 2022

(51) Int. Cl.
| | |
|---|---|
| *A61K 8/42* | (2006.01) |
| *A61K 8/06* | (2006.01) |
| *A61K 8/31* | (2006.01) |
| *A61K 8/37* | (2006.01) |
| *A61K 8/892* | (2006.01) |
| *A61Q 19/02* | (2006.01) |
| *A61Q 19/08* | (2006.01) |

(52) U.S. Cl.
CPC ............... *A61K 8/42* (2013.01); *A61K 8/06* (2013.01); *A61K 8/31* (2013.01); *A61K 8/37* (2013.01); *A61K 8/892* (2013.01); *A61Q 19/02* (2013.01); *A61Q 19/08* (2013.01)

(58) Field of Classification Search
CPC ........................................................ A61Q 19/02
See application file for complete search history.

(56) References Cited

U.S. PATENT DOCUMENTS

| | | | |
|---|---|---|---|
| 6,945,952 B2 | 9/2005 | Kwon | |
| 10,449,133 B1* | 10/2019 | Faig | ............ A61K 8/34 |
| 2005/0065463 A1 | 3/2005 | Tobinaga et al. | |
| 2007/0202203 A1 | 8/2007 | Amar | |
| 2015/0250707 A1 | 9/2015 | Lee | |
| 2015/0335560 A1 | 11/2015 | Bernard et al. | |
| 2016/0206546 A1 | 7/2016 | Fernandes et al. | |
| 2017/0151538 A1 | 6/2017 | Balooch et al. | |
| 2017/0172903 A1 | 6/2017 | El Akkari et al. | |
| 2017/0348221 A1 | 12/2017 | Maruyama et al. | |
| 2018/0280270 A1 | 10/2018 | Rughani et al. | |
| 2020/0276099 A1 | 9/2020 | Robbins et al. | |
| 2021/0093539 A1* | 4/2021 | LaRosa | ................... A61K 8/67 |

FOREIGN PATENT DOCUMENTS

| | | | | |
|---|---|---|---|---|
| FR | 2847816 A1 | 6/2004 | | |
| WO | 2004000389 A2 | 12/2003 | | |
| WO | 2006053790 A1 | 5/2006 | | |
| WO | WO2006053790 A1 * | 5/2006 | ............. | A61Q 17/00 |
| WO | 2008053198 A1 | 5/2008 | | |
| WO | 2012131623 A2 | 10/2012 | | |
| WO | WO2012131623 A2 * | 10/2012 | ............. | A61B 18/20 |
| WO | 2013088368 A2 | 6/2013 | | |

OTHER PUBLICATIONS

World Health Organization, Radiation: Effects of ultraviolet (UV) radiation on the skin, eyes and immune system, publication date: Sep. 17, 2003 (Year: 2003).*
Murat Reis Akkaya, Prediction of fatty acid composition of sunflower seeds by near-infrared reflectance spectroscopy, J Food Sci Technol (Jun. 2018) 55(6):2318-2325 (Year: 2018).*
Yasemin Oram et al, The Journal of Clinical and Aesthetic Dermatology, vol. 7, No. 3, Mar. 2014 (Year: 2014).*
ECHA, An agency of the European Union, Substance Infocard, N-Acétyl-3-Trifluorométhyl-Phényl-(Valine-Glycine), Last updated date: Dec. 21, 2021 (Year: 2021).*
Kumar Metal Industries, Shea Butter: Properties and applications, downloaded in Nov. 2023 (Year: 2023).*
Preliminary Search Report and Written Opinion issued on Mar. 18, 2022 for corresponding FR Application No. FR 2105014.
Database GNPD, Mintel; Anonymous: "Eye Cream," 2021 XP055902004.

* cited by examiner

*Primary Examiner* — Mark V Stevens
*Assistant Examiner* — Alparslan Asan
(74) *Attorney, Agent, or Firm* — POLSINELLI PC

(57) ABSTRACT

A method for managing skin tone comprising reducing the synthesis of melanin by applying a skin treatment composition to skin. The skin treatment composition may include about 0.1 to about 25 wt. % of acetyl trifluoromethylphenyl valylglycine; about 0.5 to about 30 wt. % of a polyol; about 0.1 to about 30 wt. % of a silicone, fatty compound, or a mixtures thereof, wherein the skin treatment composition is an emulsion, and all weight percentages are based on the total weight of the skin treatment composition.

18 Claims, 5 Drawing Sheets

METHODS AND COMPOSITIONS FOR IMPROVING SKIN

FIELD OF THE DISCLOSURE

The instant disclosure relates to skin treatment compositions and methods for improving skin tone using such skin treatment compositions.

BACKGROUND OF THE DISCLOSURE

Products for managing skin tone, and in some cases reducing skin tone discoloration, have become popular. In particular, consumers desire products for reducing skin tone discoloration associated with dyschromia, such as freckles, age spots, lentigines, melasma, age spots, liver spots, and chloasma.

It is conventionally believed that expressions of dyschromia are the result of or are at least partly induced by the skin's exposure to the sun light. For example, ultraviolet (UV) light speeds up the production of melanin, a natural pigment that gives skin its color. While many consumers utilize products to protect their skin from UV radiation produced by the sun, over 90% of solar energy is from visible light and infrared (IR) radiation. Visible light and IR radiation, especially IRA (770-1400 nm), penetrates deep into human skin than UV radiation, and can easily reach the dermis. Visible light, especially high energy visible light, can induce pigmentation in a similar manner as UVA.

Accordingly, there is an ongoing need for skin treatment compositions and methods for managing skin tone.

SUMMARY OF THE DISCLOSURE

The instant disclosure relates to skin treatment compositions and methods for managing skin tone using such skin treatment compositions. According to certain aspects of the disclosure, methods and skin treatment compositions disclosed herein may be used to advantageously enhance skin tone consistency and/or reduce skin tone discoloration. Additionally, the skin treatment compositions may reduce inflammation of skin, e.g., resulting from eczema, acne, and psoriasis, which has been a relatively difficult effect to traditionally achieve. In some cases, the skin treatment compositions and methods of use may be useful for reducing under eye dark circles, which is an unexpected effect.

A method for managing skin tone according to an aspect of the disclosure typically comprises:
  (a) reducing the synthesis of melanin by applying a skin treatment composition to skin, the skin treatment comprising:
    (i) about 0.1 to about 25 wt. % of acetyl trifluoromethylphenyl valylglycine; and
    (ii) optionally, about 0.1 to about 90 wt. % of a silicone, fatty compound, or a mixtures thereof,
      wherein all weight percentages are based on the total weight of the skin treatment composition.

Preferably, the method reduces the synthesis of melanin by about 5% or more. For example, the method may reduce the synthesis of melanin by about 15% or more. The method may include applying the skin treatment composition at least twice a day. In some cases, the skin treatment composition is applied at least once a day for about 20 or more days.

The method may further comprise a step of inducing melanin synthesis in the skin before the step of reducing the synthesis of melanin by applying the skin treatment composition to skin. For example, a skin procedure may be applied to the skin, which induces melanin synthesis, before the application of the skin treatment composition. The melanin synthesis may, additionally or alternatively, be induced by an inflammatory response in the skin. In some cases, the method may induce melanin synthesis and/or skin dyschromia using a procedure selected from a laser procedure, a microneedle procedure, a cryotherapy procedure, a radiofrequency microneedle procedure, or a combination thereof. In other cases, the method may induce melanin synthesis and/or skin dyschromia using an at-home procedure selected from a microneedle procedure, a light therapy procedure (e.g., red and/or blue light), a high frequency procedure, or a combination thereof. The method may comprise reducing the synthesis of melanin in skin under the eye, e.g., to reduce the appearance of under eye dark circles.

According to another aspect of the disclosure, a method is provided for treating skin having one or more of eczema, acne, and psoriasis, the method comprising:
  (a) reducing inflammation of the skin having one or more of eczema, acne, or psoriasis by applying an amount of skin treatment composition, the skin treatment composition comprising:
    (i) about 0.1 to about 25 wt. % of acetyl trifluoromethylphenyl valylglycine; and
    (ii) optionally, about 0.1 to about 90 wt. % of a silicone, fatty compound, or a mixtures thereof,
      wherein all weight percentages are based on the total weight of the skin treatment composition.

The method may include applying an effective amount of the skin treatment composition to the skin. In some cases, the amount of acetyl trifluoromethylphenyl valylglycine is applied to the skin is about 0.1 to about 9 g/dm$^2$. The methods described herein may include applying a skin treatment composition that further comprises about 0.5 to about 30 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

In accordance with yet another aspect, provided is a skin treatment composition typically including:
  (i) about 0.1 to about 25 wt. % of acetyl trifluoromethylphenyl valylglycine;
  (ii) about 0.1 to about 90 wt. % of a silicone, fatty compound, or a mixtures thereof,
    wherein the skin treatment composition is an emulsion, the skin treatment compositions being formulated to synthesis of melanin in the epidermis layer of skin, and all weight percentages are based on the total weight of the skin treatment composition.

The skin treatment composition may include: (iii) about 0.5 to about 30 wt. % of a polyol chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

Additionally or alternatively, the skin treatment composition may have about 0.1 to about 30 wt. % of a fatty compound chosen from a fatty alcohol, a fatty ester, a fatty ether, a fatty acid, a hydrocarbon oil, derivatives thereof, or mixtures thereof. Non-limiting examples of fatty compounds include fatty alcohols chosen from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, cis-4-t-butylcyclohexanol, isotridecyl alcohol, myricyl alcohol, arachidyl alcohol, and mixtures thereof. The fatty compound may be a plant based hydrocarbon oil chosen from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and mixtures thereof.

The skin treatment composition may have about 0.1 to about 30 wt. % of a silicone chosen from lauryl peg-9 polydimethylsiloxyethyl dimethicone, dimethylsiloxane, polydimethylsiloxane, polydimethylsiloxane, dimethicone, acrylate/dimethicone polymer, and mixtures thereof.

In some cases, the skin treatment composition includes about 0.1 to about 15 wt. % of a skin active agent. Non-limiting examples of skin active agents include those chosen from sodium hyaluronate, capryloyl salicylic acid, coco-caprylate/caprate, alpha and/or beta arbutin, ferulic acid, lucinol, kojic acid, resorcinol, tranexamic acid, gentisic acid, homogentisic, methyl gentisate or homogentisate, dioic acid, D pantheteine calcium sulphonate, lipoic acid, ellagic acid, vitamin B3, linoleic acid, stilbenoid, coumarin, tannin, curcuminoid, chalcone, phenylpropanoid, anthocyanin, dihydrochalcone, anthocyanidin, tocopherols, sesame lignin, vitamin C, derivatives thereof, salts thereof, or mixtures thereof. The skin treatment compositions may be used in methods for treating and/or alleviating skin suffering from one or more of eczema, acne, and psoriasis.

BRIEF DESCRIPTION OF THE FIGURES

Implementation of the present technology will now be described, by way of example only, with reference to the attached figures, wherein.

Figure 1:
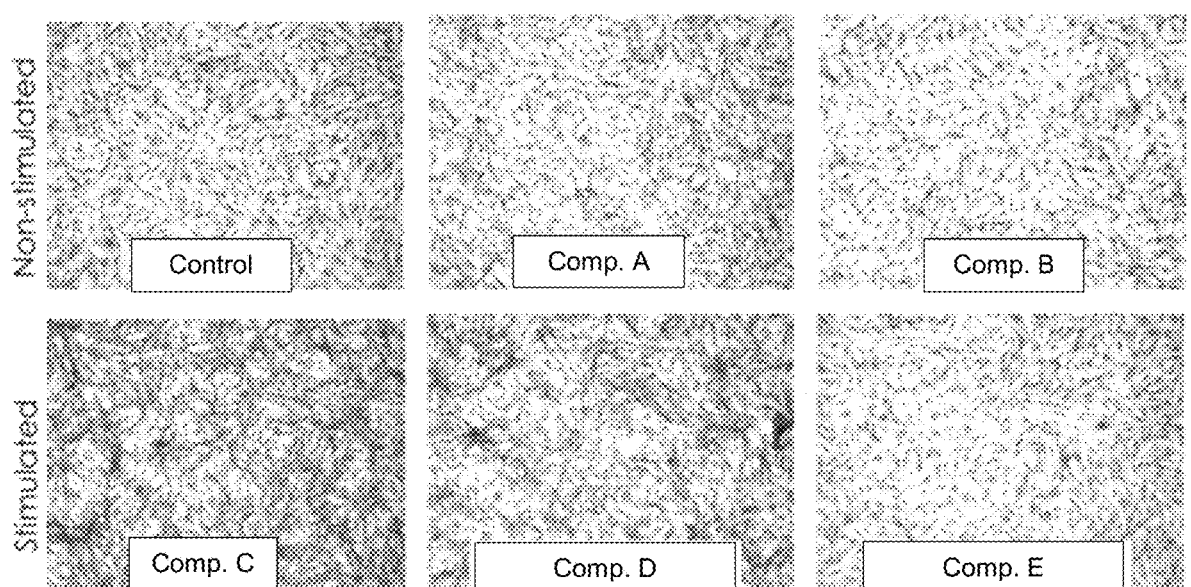
FIG. 1 is images of in vitro skin cells illustrating the melanin synthesis after applications of various compositions in accordance with aspects of the disclosure.

It should be understood that the various aspects are not limited to the arrangements and instrumentality shown in the drawings.

DETAILED DESCRIPTION OF THE DISCLOSURE

The instant disclosure relates to methods and skin treatment compositions for managing skin tone. The methods and skin treatment compositions may desirably provide enhanced skin tone consistency and/or reduce skin tone discoloration. For example, the methods and skin treatment compositions may reduce dyschromia, such as freckles, age spots, lentigines, melasma, age spots, liver spots, and/or chloasma.

The inventors were surprised that the methods and skin treatment compositions may also reduce inflammation of skin, e.g., resulting from eczema, acne, and psoriasis, which has been a relatively difficult effect to traditionally achieve. In some cases, the skin treatment compositions and methods of use may reduce under eye dark circles, which is an unexpected effect.

A method for managing skin tone according to an aspect of the disclosure typically comprises:

(a) reducing the synthesis of melanin by applying a skin treatment composition to skin, the skin treatment comprising:

(i) about 0.1 to about 25 wt. % of acetyl trifluoromethylphenyl valylglycine; and (ii) optionally, about 0.1 to about 90 wt. % of a silicone, fatty compound, or a mixtures thereof, wherein all weight percentages are based on the total weight of the skin treatment composition.

The methods for managing skin tone typically include reducing the synthesis of melanin in the epidermis layer of skin. For example, the methods generally include applying a skin treatment composition to skin to reduce the amount melanin synthesized by melanocytes cells in the epidermis layer. Surprisingly, in some instances, the methods and skin treatment compositions are effective in reducing the synthesis of melanin that has been induced by an external factor. Such external factors that may induce melanin synthesis include, but are not limited to, skin treatment procedures directed to encouraging or inducing skin cell growth and/or repair, exposure of the skin to sun light, and exposure of melanocytes cells to certain chemicals. In some instances, melanin synthesis may be induced by inflammatory responses of the skin.

By way of example, the methods and skin treatment compositions may be effective in reducing the amount melanin synthesized in response to inducement from skin treatment procedures. The skin treatment procedures may be performed by a professional or may be an at-home skin treatment procedures performed by the user. Examples of professional skin treatment procedures include laser procedures, microneedle procedures, cryotherapy procedures, radiofrequency microneedle procedures, or combinations thereof. Examples of at-home skin treatment procedures include microneedle procedures, light therapy procedures (e.g., near infrared red light and/or near ultraviolet blue light), high frequency procedures, or a combination thereof.

Additionally, the inventors were surprised that certain methods and skin treatment compositions disclosed herein provide a significant reduction in inflammation of the skin. For example, certain methods and skin treatment compositions may be useful for reducing inflammation of skin suffering from one or more of eczema, acne, and psoriasis. Accordingly, in accordance with another aspect of the disclosure, provided are methods for treating skin having one or more of eczema, acne, and psoriasis, the method comprising:

(a) reducing inflammation of the skin having one or more of eczema, acne, and psoriasis by applying an amount of skin treatment composition, the skin treatment composition comprising:

(i) about 0.1 to about 25 wt. % of acetyl trifluoromethylphenyl valylglycine; and (ii) optionally, about 0.1 to about 90 wt. % of a silicone, fatty compound, or a mixtures thereof, wherein all weight percentages are based on the total weight of the skin treatment composition.

In accordance with yet a further aspect of the disclosure, provided is a use of the skin treatment compositions disclosed herein for skin having one or more of eczema, acne, and psoriasis. For example, according to one embodiment, provided is a use of a skin treatment composition for skin having one or more of eczema, acne, and psoriasis comprising:

(a) reducing inflammation of the skin having one or more of eczema, acne, and psoriasis by applying an amount of skin treatment composition, the skin treatment composition comprising:
   (i) about 0.1 to about 25 wt. % of acetyl trifluoromethylphenyl valylglycine; and
   (ii) optionally, about 0.1 to about 90 wt. % of a silicone, fatty compound, or a mixtures thereof,
      wherein all weight percentages are based on the total weight of the skin treatment composition.

According to another aspect of the disclosure, provided is a use of the skin treatment compositions disclosed herein for managing skin tone. In one embodiment, provided is a use of a skin treatment composition for managing skin tone comprising:

(a) reducing the synthesis of melanin by applying a skin treatment composition to skin, the skin treatment comprising:
   (i) about 0.1 to about 25 wt. % of acetyl trifluoromethylphenyl valylglycine; and
   (ii) optionally, about 0.1 to about 90 wt. % of a silicone, fatty compound, or a mixtures thereof,
      wherein all weight percentages are based on the total weight of the skin treatment composition.

A more detailed description of skin treatment procedures that may be applied to skin before or as part of the methods for managing skin tone and/or reducing inflammation is provided below.

The skin treatment procedure may be a laser procedure that is ablative or non-ablative and, in some cases, may be fractional or non-fractional laser procedures. For example, the laser procedure may use a fractional laser that is non-ablative. Typically, skin treatment procedures that utilize a laser are performed by a professional.

A fractional laser affects the surface of the stratum corneum to create, by local photothermo lysis, a plurality of spaced-apart pores (microwells) in the upper layers of the skin. Preferably, to fractionate the impacts of the laser and space them out over the skin, preferably evenly spaced, the laser system may comprise a motorized scanner that comprises one or more rotary mirrors whose rotation speed causes scanning of the laser spot. Depending on the fractional laser used, the scanning may take place along different paths: circular, rectangular or square scanning, or random scanning. The fractional laser treatment may comprise several successive passes of the laser over a given area so as to obtain better homogeneity of the treatment. On each pass, new points of impact are created, spaced from the previous points of impact. An example of a non-ablative fractional laser is the machine sold by the company Solta under the brand name Fraxel re:store® Dual (1927 nm). Additional examples of fractional lasers are described in U.S. patent application no. 2008/0208179, which is incorporated herein in its entirety for all purposes.

The wavelength of the fractional laser may be in the inferred (IR) range. For example, the laser procedure may use a fractional laser having a wavelength of about 1100 nm to about 2500 nm, preferably about 1400 to about 200, or preferably about 1430 to about 1950. The treatment depth may be from about 200 μm to about 1.4 mm. In some instances, the treatment depth is from about 550 μm to about 1.4 mm, about 800 μm to about 1.4 mm, or about 1120 μm to about 1.4 mm.

A greater treatment depth and wider wells are obtained when the light power is stronger. The size of a microwell may range, for example, from about 0.5 μm in diameter to about 500 μm in diameter, or from about 50 μm to about 350 μm. The density of the microwells (also known as pores) created by the laser procedure may be from about 100 to about 10,000 microwells per square centimeter ($cm^2$). In some cases, the density of the microwells per square centimeter is from about 100 to about 9,000, about 100 to about 8,000, about 100 to about 7,000, about 100 to about 6,000, about 100 to about 5,000, about 100 to about 4,000, about 100 to about 3,000, about 100 to about 2,000, or about 100 to about 1,000.

The irradiance, which measures the power density received by the skin to be treated, is preferably from about 25 $kW/cm^2$ to about 4 $MW/cm^2$. The fluence of the laser treatment, which measures the energy density received on the area of skin to be treated, is preferably from about 4 $kJ/cm^2$ to about 160 $kJ/cm^2$. The energy of a laser pulse to create a microwell may range from about 0.1 mJ to about 50 mJ.

Additional description of laser procedures may be found in U.S. patent publication no. 2008/0208179 and PCT publication no. WO 2008/053198, which are incorporated herein in their entirety for all purposes.

The methods may, additionally or alternatively, utilize a microneedle procedure before or as part of the methods disclosed herein. The microneedles may be solid (e.g., hollow needles or not hollow needles), for the purpose of microperforation, or soluble, enabling the ends to break off after perforation and formation of microimplants with gradual dissolution over time. The microneedles may, thus, comprise an orifice for administering a skin treatment composition as described herein, or may be devoid of an orifice. In some instances, the microneedles may be used as skin microperforators, facilitating the subsequent application of one or more active agents. Examples of microneedles and microneedle procedures are described in PCT patent publication no. WO 2007/061964; PCT patent publication no. WO 2004/000389; U.S. Pat. No. 6,945,952; PCT patent publication no. WO 2004/024224; Japanese patent publication no. 2005/154321; PCT patent publication no. 2007/023167; U.S. patent publication no. 2005/065463; PCT patent publication no. WO 03/092785; Japanese patent publication no. 2005/154321; PCT patent publication no. WO 2007/023167; U.S. patent publication no. 2005/065463; and PCT patent publication no. WO 03/092785, which are all incorporated herein for all purposes in their entirety.

In some cases, the methods disclosed herein may use a radiofrequency microneedle procedure before or as part of the methods disclosed herein. Radiofrequency microneedle procedures may utilize one or more electrodes, such as monopolar RF electrodes, imparting perforations into one or more tissue layers of the skin. The electrodes are typically provided in a pattern to impart a corresponding pattern of perforations in one or more tissue layers. Further description of radiofrequency microneedle devices and procedures thereof are described in European patent no. 1742590; U.S. Pat. Nos. 8,317,782; and 6,277,116, which are all incorporated herein for all purposes in their entirety.

Additionally or alternatively, the methods disclosed herein may use a cryotherapy microneedle procedure before or as part of the methods disclosed herein. The cryotherapy microneedle procedures may either cool or heat the skin to damage and reduce the skin barrier function. For instance, the cryotherapy microneedle procedure may apply electromagnetic waves in a pulsed mode or in a continuous mode to reduce the skin barrier function. Additional description of cryotherapy microneedle procedures and devices thereof may be found in U.S. Pat. Nos. 8,548,599 and 7,367,341, which are both incorporated herein for all purposes in their entirety.

The methods disclosed herein may use a light therapy procedure before or as part of the methods disclosed herein. The light therapy procedure may be an at-home procedure or a professional procedure. Light therapy procedures typically include photomodulation using narrowband, multichromatic light using low-energy sources, such as light-emitting diode (LED) arrays. As illustrated in U.S. Pat. No. 6,663,659, which is incorporated herein for all purposes in its entirety, light therapy procedures have been shown to accelerate wound healing, improve many skin-related disorders, and reduce wrinkles, fine lines, and scars. At the cellular level, the use of light at low energy fluences may generate significant biological effects, including cellular proliferation, collagen synthesis, and the release of growth factors from cells. Light therapy procedures, such as intense light pulse therapy procedures have, may be useful for treating moderate to severe melasma and excessive skin pigmentation when combined with skin treatment compositions. Further discussion of light therapy as a mean to modulate skin melasma can be found in U.S. Pat. Nos. 7,886,748 and 5,290,273, which are both incorporated herein in their entireties for all purposes. A general discussion of light therapy procedures may be found in U.S. Pat. No. 9,192,780, which is incorporated herein for all purposes in its entirety.

The skin treatment procedure may be a high frequency procedure that is applied to skin before or as part of the methods disclosed herein. High frequency procedures often use electromagnetic radiation for targeted remodeling adipose tissue, focused treatment of cellulite, body contouring, skin tightening, and/or skin rejuvenation. For example, the high frequency procedures may use electromagnetic waves to heat targeted tissue to obtain a desired outcome. Examples of high frequency procedures may be found in U.S. Pat. Nos. 10,124,187 and 10,441,346, which are incorporated herein in their entirety for all purposes.

The methods for improving skin typically include applying a skin treatment composition to the skin within 24 hours of the skin treatment procedure. In some cases, it is preferable that the skin treatment composition is applied within about 20 hours, within about 16 hours, within about 12 hours, within about 10 hours, within about 8 hours, within about 6 hours, within about 4 hours, within about 2 hours, within about 1 hour after the application of the skin treatment procedure. Additionally or alternatively, the skin treatment composition may be applied before the application of the skin treatment procedure to the skin. For example, the skin treatment composition may applied within 24 hours, within about 20 hours, within about 16 hours, within about 12 hours, within about 10 hours, within about 8 hours, within about 6 hours, within about 4 hours, within about 2 hours, within about 1 hour before the application of the skin treatment procedure.

The methods may preferably include applying the skin treatment composition to the skin more than one time before or after the application of the skin treatment procedure. In some cases, the skin treatment composition is applied at least twice over a period of a month. In further cases, the skin treatment composition is applied at least three times, at least four times, at least five times, at least six times, at least seven times, at least eight times, at least nine times, or at least ten times over a period of time (e.g., one week, two weeks, three weeks, a month, two months, three months, etc.). The method may include applying the skin treatment a plurality of times (e.g., one, two, three, four, five, or six times) each day for a period of time (e.g., one week, two weeks, three weeks, a month, two months, three months, etc.).

Additionally or alternatively, the methods for improving skin may include applying an amount of the skin treatment composition such that about 0.1 gram or more of acetyl trifluoromethylphenyl valylglycine is applied to the skin. For example, the skin treatment composition may be applied such that about 0.1 gram per decimeter ($g/dm^2$) or more, about 0.5 $g/dm^2$ or more, about 07.5 $g/dm^2$ or more, about 1 $g/dm^2$ or more, about 1.5 $g/dm^2$ or more, about 2 $g/dm^2$ or more, about 2.5 $g/dm^2$ or more, or about 3 $g/dm^2$ or more of acetyl trifluoromethylphenyl valylglycine is applied to the skin. In some cases, the, the skin treatment composition is applied such that about 0.1 to about 10 gram per decimeter ($g/dm^2$), about 0.1 to about 9 $g/dm^2$, about 0.1 to about 8 $g/dm^2$, about 0.1 to about 7 $g/dm^2$, about 0.1 to about 6 $g/dm^2$, about 0.1 to about 5 $g/dm^2$, about 0.1 to about 4 $g/dm^2$, about 0.1 to about 3 $g/dm^2$, about 0.1 to about 2 $g/dm^2$, about 0.1 to about 1 $g/dm^2$; about 0.5 to about 10 gram per decimeter ($g/dm^2$), about 0.5 to about 9 $g/dm^2$, about 0.5 to about 8 $g/dm^2$, about 0.5 to about 7 $g/dm^2$, about 0.5 to about 6 $g/dm^2$, about 0.5 to about 5 $g/dm^2$, about 0.5 to about 4 $g/dm^2$, about 0.5 to about 3 $g/dm^2$, about 0.5 to about 2 $g/dm^2$, about 0.5 to about 1 $g/dm^2$; or about 1 to about 10 gram per decimeter ($g/dm^2$), about 1 to about 9 $g/dm^2$, about 1 to about 8 $g/dm^2$, about 1 to about 7 $g/dm^2$, about 1 to about 6 $g/dm^2$, about 1 to about 5 $g/dm^2$, about 1 to about 4 $g/dm^2$, about 1 to about 3 $g/dm^2$, or about 1 to about 2 $g/dm^2$ of acetyl trifluoromethylphenyl valylglycine is applied to the skin.

The skin treatment compositions may include various ingredient and/or components, but typically comprise:
  (i) about 0.1 to about 25 wt. % of acetyl trifluoromethylphenyl valylglycine; and
  (ii) about 0.1 to about 90 wt. % of a silicone, fatty compound, or a combination thereof,
    wherein the skin treatment composition is an emulsion, the skin treatment compositions being formulated to synthesis of melanin in the epidermis layer of skin, and all weight percentages are based on the total weight of the skin treatment composition.

The skin treatment compositions are preferably formulated to be a cream, a lotion, a serum, or an ampoule. For example, the skin treatment compositions may have water-in-oil emulsions, oil-in-water emulsions, silicone-in-water emulsions, water-in-silicone emulsions, or combinations thereof. The skin treatment compositions may be used in methods for treating and/or alleviating skin suffering from one or more of eczema, acne, and psoriasis.

In some embodiments, it may be desirable for the skin treatment composition to not be a gel (e.g., comprising or in a gel layer on a substrate). Thus, in some cases, the total amount of gelling agents/ingredients, such as water-swellable polymers and/or water-insoluble polymers, is less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt.

%, or less than about 0.5 wt. %, based on the total weight of the skin treatment compositions.

Additionally or alternatively, the skin treatment compositions may be transparent. The term "transparent" with respect to a transparent composition indicates that the composition has transmittance of at least 80% at a wavelength of 600 nm, for example measured using a Lambda 40 UV-visible spectrometer. The skin treatment compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

The skin treatment compositions may be formulated to have a viscosity of about 1 to about 10,000 cPs at a temperature of 24° C. as measured with RV-4 Disk spindle on a Brookfield DV2T viscometer at a range of 5-20 rpm after 90 seconds. For example, the skin treatment composition may have a viscosity of about 1 to about 10,000 cPs, about 1 to about 9,000 cPs, about 1 to about 8,000 cPs, about 1 to about 7,000 cPs, about 1 to about 6,000 cPs, about 1 to about 5,000 cPs, about 1 to about 4,000 cPs, about 1 to about 3,000 cPs, about 1 to about 2,000 cPs, about 1 to about 1,000 cPs, about 1 to about 500 cPs, about 1 to about 250 cPs, about 1 to about 100 cPs; about 100 to about 10,000 cPs, about 100 to about 9,000 cPs, about 100 to about 8,000 cPs, about 100 to about 7,000 cPs, about 100 to about 6,000 cPs, about 100 to about 5,000 cPs, about 100 to about 4,000 cPs, about 100 to about 3,000 cPs, about 100 to about 2,000 cPs, about 100 to about 1,000 cPs, about 100 to about 500 cPs, about 100 to about 250 cPs; about 500 to about 10,000 cPs, about 500 to about 9,000 cPs, about 500 to about 8,000 cPs, about 500 to about 7,000 cPs, about 500 to about 6,000 cPs, about 500 to about 5,000 cPs, about 500 to about 4,000 cPs, about 500 to about 3,000 cPs, about 500 to about 2,000 cPs, about 500 to about 1,000 cPs; about 1,000 to about 10,000 cPs, about 1,000 to about 9,000 cPs, about 1,000 to about 8,000 cPs, about 1,000 to about 7,000 cPs, about 1,000 to about 6,000 cPs, about 1,000 to about 5,000 cPs, about 1,000 to about 4,000 cPs, about 1,000 to about 3,000 cPs, about 1,000 to about 2,000 cPs; about 3,000 to about 10,000 cPs, about 3,000 to about 9,000 cPs, about 3,000 to about 8,000 cPs, about 3,000 to about 7,000 cPs, about 3,000 to about 6,000 cPs, about 3,000 to about 5,000 cPs; about 5,000 to about 10,000 cPs, about 5,000 to about 9,000 cPs, about 5,000 to about 8,000 cPs, about 5,000 to about 7,000 cPs; about 7,000 to about 10,000 cPs, about 7,000 to about 9,000 cPs, at a temperature of 24° C. as measured with RV-4 Disk spindle on a Brookfield DV2T viscometer at a range of 5-20 rpm after 90 seconds.

In some cases, the skin treatment compositions are free of or substantially free of hyaluronic acid and/or salts thereof. For instance, the skin treatment composition may include less than about 5 wt. %, less than about 4 wt. %, less than about 3 wt. %, less than about 2 wt. %, or less than about 1 wt. % of hyaluronic acid and/or salts thereof, based on the total weight of the skin treatment composition. In at least one instance, the skin treatment composition has about 0 wt. % or 0 wt. % of hyaluronic acid and/or salts thereof, based on the total weight of the skin treatment composition.

Suitable components, such as those listed below, may be included or excluded from the formulations for the skin treatment compositions depending on the specific combination of other components, the form of the skin treatment composition (e.g., a cream, a lotion, a serum, or an ampoule), and/or the use of the skin treatment composition.

Acetyl Trifluoromethylphenyl Valylglycine

The skin tightening compositions include an amount of acetyl trifluoromethylphenyl valylglycine that may vary, but typically is from about 0.1 to about 25 wt. %, based on the total weight of the skin treatment composition. For example, the amount of acetyl trifluoromethylphenyl valylglycine present in the skin treatment composition may be from about 0.1 to about 25 wt. %, about 0.1 to about 22 wt. %, about 0.1 to about 19 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 25 wt. %, about 0.25 to about 22 wt. %, about 0.25 to about 19 wt. %, about 0.25 to about 16 wt. %, about 0.25 to about 14 wt. %, about 0.25 to about 12 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 25 wt. %, about 0.5 to about 22 wt. %, about 0.5 to about 19 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 25 wt. %, about 0.75 to about 22 wt. %, about 0.75 to about 19 wt. %, about 0.75 to about 16 wt. %, about 0.75 to about 14 wt. %, about 0.75 to about 12 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 25 wt. %, about 1 to about 22 wt. %, about 1 to about 19 wt. %, about 1 to about 16 wt. %, about 1 to about 14 wt. %, about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 25 wt. %, about 2 to about 22 wt. %, about 2 to about 19 wt. %, about 2 to about 16 wt. %, about 2 to about 14 wt. %, about 2 to about 12 wt. %, about 2 to about 10 wt. %, about 2 to about 8 wt. %, about 2 to about 6 wt. %, about 2 to about 5 wt. %, about 2 to about 4 wt. %, about 2 to about 3 wt. %; about 5 to about 25 wt. %, about 5 to about 22 wt. %, about 5 to about 19 wt. %, about 5 to about 16 wt. %, about 5 to about 14 wt. %, about 5 to about 12 wt. %, about 5 to about 10 wt. %, about 5 to about 8 wt. %; about 7.5 to about 27.5 wt. %, about 7.5 to about 22 wt. %, about 7.5 to about 19 wt. %, about 7.5 to about 16 wt. %, about 7.5 to about 14 wt. %, about 7.5 to about 12 wt. %, about 7.5 to about 10 wt. %; about 10 to about 27.5 wt. %, about 10 to about 22 wt. %, about 10 to about 19 wt. %, about 10 to about 16 wt. %, about 10 to about 14 wt. %, about 10 to about 12 wt. %; about 15 to about 27.5 wt. %, about 15 to about 22 wt. %, about 15 to about 19 wt. %; about 20 to about 27.5 wt. %, about 20 to about 22 wt. %, including ranges and subranges therebetween, based on the total weight of the skin treatment composition.

Polyol(s)

The skin treatment composition may, preferably, include one or more polyols. The total amount of polyols in the skin treatment composition may vary from, e.g., about 0.5 to about 30 wt. %, based on the total weight of the skin treatment composition. For example, the total amount of polyols may be from about 0.5 to about 30 wt. %, about 0.5 to about 25 wt. %, about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 30 wt. %, about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 30 wt. %, about 4 to about 25 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %, about 5 to about 7 wt. %, about 5 to about 6 wt. %; about 7 to about 30 wt. %, about 7 to about 25 wt. %, about 7 to about 20 wt. %, about 7 to about 18 wt. %, about 7 to about 16 wt. %, about 7 to about 14 wt. %, about 7 to about 12 wt. %, about 7 to about 10 wt. %; about 10 to about 30 wt. %, about 10 to about 25 wt. %, about 10 to about 20 wt. %, about 10 to about 18 wt. %, about 10 to about 16 wt. %, about 10 to about 14 wt. %, about 10 to about 12 wt. %; about 12.5 to about 30 wt. %, about 12.5 to about 25 wt. %, about 12.5 to about 20 wt. %, about 12.5 to about 18 wt. %, about 12.5 to about 16 wt. %; about 15 to about 30 wt. %, about 15 to about 25 wt. %, about 15 to about 20 wt. %, about 15 to about 18 wt. %, or about 15 to about 16 wt. %, including all ranges and sub-ranges therebetween, based on the total weight of the skin treatment composition.

The polyols of the skin treatment composition may comprise or be chosen from polyols having from 2 to 15 carbon atoms and at least two hydroxyl groups. Exemplary polyols that may be used in the skin treatment composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The polyol(s) may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the skin treatment composition includes or is chosen from caprylyl glycol, glycerin, and a mixture thereof.

Silicone(s), Fatty Compound(s), or Mixtures Thereof

The skin treatment compositions may include one or more silicone(s), fatty compound(s), or mixtures thereof in amount that my vary, but is typically about 0.1 to about 90 wt. %, based on the total weight of the skin treatment compositions. In some instances, the amount of silicone(s), fatty compound(s), or mixtures thereof present in the skin treatment compositions is about 0.1 to about 90 wt. %, about 0.1 to about 80 wt. %, about 0.1 to about 70 wt. %, about 0.1 to about 60 wt. %, about 0.1 to about 50 wt. %, about 0.1 to about 40 wt. %, about 0.1 to about 30 wt. %, about 0.1 to about 25 wt. %, about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to about 90 wt. %, about 0.5 to about 80 wt. %, about 0.5 to about 70 wt. %, about 0.5 to about 60 wt. %, about 0.5 to about 50 wt. %, about 0.5 to about 40 wt. %, about 0.5 to about 30 wt. %, about 0.5 to about 25 wt. %, about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 90 wt. %, about 1 to about 80 wt. %, about 1 to about 70 wt. %, about 1 to about 60 wt. %, about 1 to about 50 wt. %, about 1 to about 40 wt. %, about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 90 wt. %, about 2 to about 80 wt. %, about 2 to about 70 wt. %, about 2 to about 60 wt. %, about 2 to about 50 wt. %, about 2 to about 40 wt. %, about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 90 wt. %, about 3 to about 80 wt. %, about 3 to about 70 wt. %, about 3 to about 60 wt. %, about 3 to about 50 wt. %, about 3 to about 40 wt. %, about 3 to about 30 wt. %, about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 90 wt. %, about 4 to about 80 wt. %, about 4 to about 70 wt. %, about 4 to about 60 wt. %, about 4 to about 50 wt. %, about 4 to about 40 wt. %, about 4 to about 30 wt. %, about 4 to about 25 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 90 wt. %, about 5 to about 80 wt. %, about 5 to about 70 wt. %, about 5 to about 60 wt. %, about 5 to about 50 wt. %, about 5 to about 40 wt. %, about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %, about 5 to about 7 wt. %, about 5 to about 6 wt. %; about 7.5 to about 90 wt. %, about 7.5 to about 80 wt. %, about 7.5 to about 70 wt. %, about 7.5 to about 60 wt. %, about 7.5 to about 50 wt. %, about 7.5 to about 40 wt. %, about 7.5 to about 30 wt. %, about 7.5 to about 25 wt. %, about 7.5 to about 20 wt. %, about 7.5 to about 18 wt. %, about 7.5 to about 16 wt. %, about 7.5 to about 14 wt. %, about 7.5 to about 12 wt. %, about 7.5 to about 10 wt. %; about 10 to about 90 wt. %, about 10 to about 80 wt. %, about 10 to about 70 wt. %, about 10 to about 60 wt. %, about 10 to about 50 wt. %, about 10 to about 40 wt. %, about 10 to about 30 wt. %, about 10 to about 25 wt. %, about 10 to about 20 wt. %, about 10 to about 18 wt. %, about 10 to about 16 wt. %, about 10 to about 14 wt. %, about 10 to about 12 wt. %; about 12.5 to about 90 wt. %, about 12.5 to about 80 wt. %, about 12.5 to about 70 wt. %, about 12.5 to about 60 wt. %, about 12.5 to about 50 wt. %, about 12.5 to about 40 wt. %, about 12.5 to about 30 wt. %, about 12.5 to about 25 wt. %, about 12.5 to about 20 wt. %, about 12.5 to about 18 wt. %, about 12.5 to about 16 wt. %; about 15 to about 90 wt. %, about 15 to about 80 wt. %, about 15 to about 70 wt. %, about 15 to about 60 wt. %, about 15 to about 50 wt. %, about 15 to about 40 wt. %, about 15 to about 30 wt. %, about 15 to about 25 wt. %, about 15 to about 20 wt. %, about 15 to about 18 wt. %, or about 15 to about 16 wt. %, including all ranges and sub-ranges therebetween, based on the total weight of the skin treatment composition.

Silicone(s)

The skin treatment compositions may include one or more silicones. The silicones may, optionally, be functionalized with an amino group or functionalized with a methacrylic group. The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The skin treatment composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

One or more silicone(s) may be included in the skin treatment composition has an emulsifier. For example, the silicone may be an organosiloxane emulsifier, oxyalkylenated organosiloxane emulsifier, PEGylated organic siloxane emulsifiers, or a cross-linked organosiloxane emulsifiers. Although not specifically identified, some of the silicones listed below may be utilized as emulsifiers.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

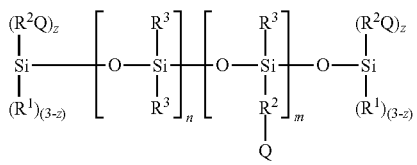

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from —$NR^4_2$ and —$NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, —$CH_2CH(CH_3)CH_2$— and —$CH_2CH_2CH(CH_3)CH_2$—. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

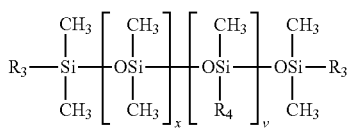

wherein $R_3$ is hydroxyl or $OR_5$, $R_5$ is a $C_1$ to $C_4$ alkyl group, $R_4$ is a group with structure according to the following formula:

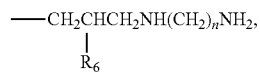

$R_6$ is a $C_1$ to $C_4$ alkyl, n is a 1 to 4, x is the same as "n" described above, and y is the same as "m" described above.

The silicone may be a polysiloxane corresponding to the following formula:

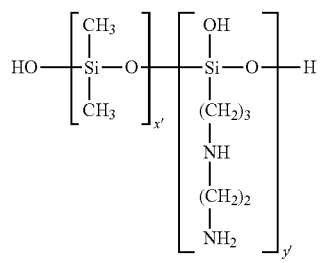

in which x' and y' are integers such that the weight-average molecular weight (Mw) is comprised between about 5000 and 500 000;

b) amino silicones corresponding to following formula:

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$CqH_2qL$ in which q is a number ranging from 2 to 8 and L is an optionally quaternized amino group chosen from the following groups:

—NR"-Q-N(R")$_2$
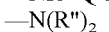
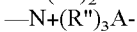
—N+(R")$_3$A-
—N+H(R")$_2$A-
—N+H$_2$(R") A-
—N(R")-Q-N+R"H$_2$A-
—NR"-Q-N+(R")$_2$HA-
—NR"-Q-N+(R")$_3$A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

Another group of amino silicones corresponding to this definition is represented by silicones having the following formula:

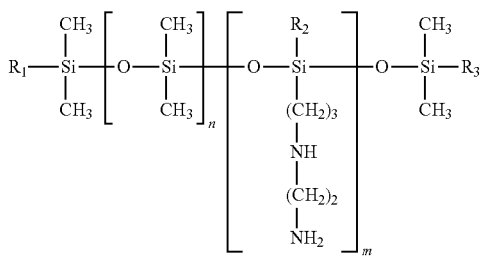

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

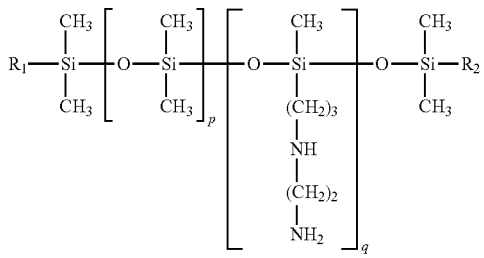

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

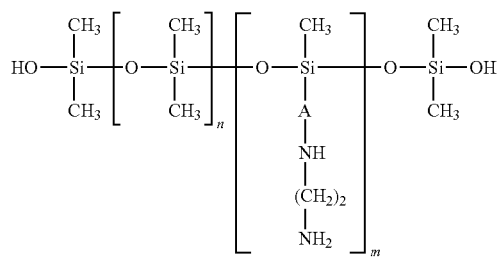

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear. The weight-average molecular weight (Mw) of these amino silicones ranges preferably from 2000 to 1 000 000 and even more particularly from 3500 to 200 000.

Another group of amino silicones is represented by the following formula:

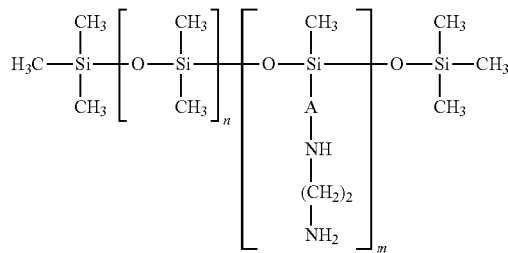

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched. The weight-average molecular weight (Mw) of these amino silicones ranges preferably from 500 to 1 000 000 and even more particularly from 1000 to 200 000.

Another group of amino silicones is represented by the following formula:

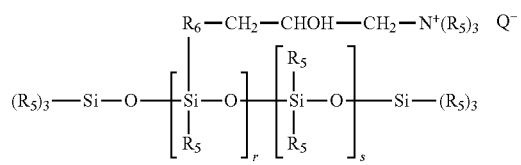

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50. Such amino silicones are described more particularly in U.S. Pat. No. 4,185,087, which is incorporated herein in its entirety for all purposes.

A group of quaternary ammonium silicones is represented by the following formula:

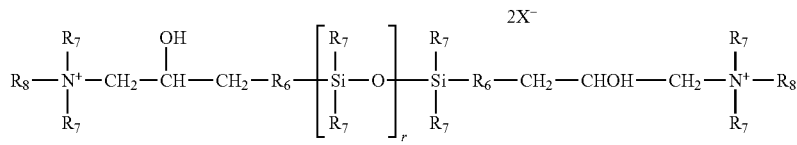

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X— is an anion such as a halide ion, in particular chloride, or an organic acid salt (for example acetate);

r represents a mean statistical value from 2 to 200 and in particular from 5 to 100. These silicones are described, for example, in European patent application no. 0530974, which is incorporated herein in its entirety for all purposes.

A group of quaternary ammonium silicones is represented by the following formula:

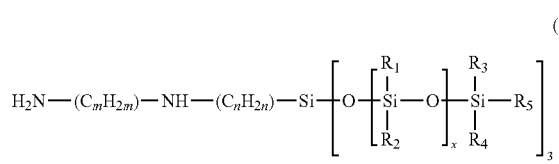 (J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

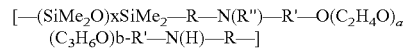

or alternatively

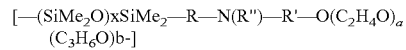

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—. The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]terminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the skin treatment compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Fatty Compound(s)

Examples of fatty compound(s) that may be incorporated into the skin treatment composition include fatty alcohol, a fatty ester, a fatty ether, a fatty acid, a wax, an oil, a derivative thereof, and a mixture thereof. Additional examples of fatty compounds that are worth mentioning include oils, mineral oil, alkanes (paraffins), fatty alcohol derivatives, fatty acid derivatives, esters of fatty alcohols, hydroxy-substituted fatty acids, waxes, triglyceride compounds, lanolin, and a mixture thereof. One or more fatty compounds(s) may be included in the skin treatment composition has an emulsifier. For example, the fatty compound may be a fatty alcohol that is capable of or is used for emulsifying another ingredient. Although not specifically identified, some of the fatty compounds listed below may be utilized as emulsifiers. Further examples of fatty compounds are discussed below.

(i) Fatty Ester(s)

The skin treatment compositions may include one or more fatty compound(s) that is a fatty ester. For example, the fatty compound(s) may be chosen from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof.

Additionally or alternatively, the fatty ester chosen from cetyl ester, purcellin oil (cetearyl octanoate), isopropyl myristate, isopropyl palmitate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

(ii) Fatty Alcohol(s)

Suitable fatty alcohols, if present, include those having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

(iii) Fatty Ether(s)

The fatty compounds may be chosen from fatty ethers. For example, the skin treatment composition may include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, or a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

(iv) Fatty Acid(s)

In some instances, the fatty compounds may be chosen from fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

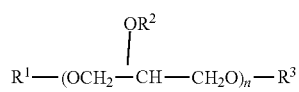

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

(v) Wax(es)

The fatty compounds may, in some instances, include or be chosen from one or more waxes. Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (Helianthus annuus), carnauba, candelilla, ouricury or japan wax or cork fibre or sugarcane waxes), or a mixture thereof.

(vi) Oil(s)

The skin treatment compositions include one or more oils. The oil component of the NLCs is typically has melting temperature of less than 45° C., a molecular weight of at least 190, and a solubility in water of no greater than 1 part in 99 parts of water.

Non-limiting examples of include, but are not limited to, natural oils, such as coconut oil; hydrocarbons, such as mineral oil and hydrogenated polyisobutene; esters, such as $C_{12}$-$C_{15}$ alkyl benzoate; diesters, such as propylene dipelarganate; and triesters, such as glyceryl trioctanoate. Further examples of oils that may, optionally, be included in the skin treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Additionally or alternatively, the oil may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, Ricinus communis (castor) seed oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Skin Active Agent(s)

The skin tightening compositions may, optionally, include one or more skin active agents, such as anti-aging agent, anti-wrinkle actives, anti-oxidants, humectants, moisturizing ingredients, depigmenting agents, and/or agents for treating oily skin etc. The skin active agents may be included in the skin tightening composition in an amount ranging from greater than zero to about to about 10 wt. %, based on the total weight of the composition. For example, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, including ranges and subranges therebetween, based on the total weight of the skin tightening composition.

A non-limiting discussion of skin active agents that may, in some cases, be included in the skin tightening composition is provided below:

Humectants and/or Moisturizing Ingredients

Examples of humectants and/or moisturizing ingredients include glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting Agents Other than Acetyl Trifluoromethylphenyl Valylglycine

Depigmenting agents that may be incorporated in the skin tightening composition include those chosen from alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (vera, ferox, bardensis), mulberry, skullcap, a water kiwi fruit (Actinidia chinensis) marketed by Gattefosse, an extract of Paeonia suffruticosa root, such as that sold by Ichimaru Pharcos under the name Liquid Botanpi Be an extract of brown sugar (Saccharum officinarum) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (Actinidia chinensis) marketed by Gattefosse, an extract of Paeonia suffruticosa root, such as that sold by the company Ichimaru Pharcos under the name Botanpi Liquid B.

Anti-Wrinkle Active

The skin tightening composition may include one or more anti-wrinkle actives. The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the α-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxyethyl) phenethyl-amino-5'- —N-ethylcarboxamido adenosine (CGS-21680), N-ethylcarboxam ido-adenosine (NECA), the 5'(N-cyclopropyl)-carboxamidoadenosine, DPMA (PD 129.944) and metrifudil.

Antioxidants

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (Myrciaria dubia), acerola, emblica officinalis, and bioflavonoids from rose hip and citrus may be used including watersoluble bioflavonoids such as hesperidin methyl chalcone may also be used.

Sesame (Sesamum indicum) or sesame lignan may also be added. Sesame and its lignans (the fibrous compounds associated with the sesame) act as antioxidants. Sesame seed lignans significantly enhance vitamin E activity.

Other antioxidants include tocopherols (e.g. d-α-tocopherol, d-β-tocopherol, d-γ-tocopherol, d-delta-tocopherol), tocotrienols (e.g. d-α-tocotrienol, d-β-tocotrienol, d-γ.-tocotrienol, d-delta-tocotrienol,) and vitamin E (α-tocopherol acetate). These compounds may be isolated from natural sources, prepared by synthetic means, or mixtures thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids

The active agent may be an antioxidant selected from the group of flavonoids. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcum in, bis-Desmethoxycurcum in, Tetrahydrocurcum in, and Tetrahydrocurcuminoids. Curcumin and tetrahydrocurcuminoids may be derived from rhizomes of Curcuma longa. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (Sesamum indicum) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Thickening Agent(s)

The skin treatment compositions described herein may, optionally, include a thickening agent. The amount of thickening agents can vary but is typically from about 0.01 to about 20 wt. %, based on the total weight of the skin treatment composition. In some instances, the amount of fatty compounds present in the skin treatment compositions is about 0.1 to 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, about 5 to about 7 wt. %, or about 5 to about 6 wt. %, including all ranges and sub-ranges therebetween, based on the total weight of the skin treatment composition.

The thickening agent(s) may be chosen from xanthan gum, guar gum, biosaccharide gum, cellulose, acacia seneca gum, sclerotium gum, agarose, pechtin, gellan gum, hyaluronic acid. Additionally, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/$C_{10}$-30 alkyl acrylate crosspolymer. In some cases, the composition includes ammonium polyacryloyldimethyl taurate and/or sodium polyacrylate. Suitable thickening agents may be found in U.S. patent application Ser. No. 16/731,654, which is incorporated herein, in its entirety for all purposes.

Many thickening agents are water-soluble, and increase the viscosity of water or form an aqueous gel when the skin treatment composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the skin treatment compositions of the instant disclosure. Thickening agents may be referred to as "thickeners" or "viscosity modifying agents." Thickening agents are typically included to increase the viscosity of the skin treatment compositions. Nonetheless, in some instances, certain thickening agents provide additional, surprising benefits to the skin treatment compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, $C_8$-24 hydroxyl substituted aliphatic acid, $C_8$-24 conjugated aliphatic acid, sugar fatty esters, polyglyceryl esters, and a mixture thereof. Particular types of thickening agents that may be mentioned include the following:

Carboxylic Acid or Carboxylate Based Homopolymer or Co-polymer, Which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-polymers:

Non-limiting examples include Polyvinylpyrrolidone (PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters:

Non-limiting polyglycerol esters of fatty acids (polygylceryl esters) include those of the following formula:

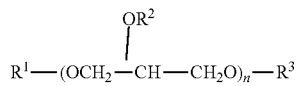

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

pH Adjuster(s)

The skin treatment composition may include one or more pH adjusters to increase or decrease the overall pH of the skin treatment composition. For example, one or more acids may be included to decrease the pH of the skin treatment composition. Examples of suitable acids for decreasing the pH of the skin treatment composition include, but are not limited to, citric acid, acetic acid, and the like. The skin treatment composition may include one or more bases, such as sodium hydroxide, potassium hydroxide and the like, to increase the pH of the skin treatment composition. Additional or alternative acids and bases that are suitable for adjusting the pH of the skin treatment composition are readily known to one of ordinary skill in the art.

The amount of the pH adjuster in the skin treatment composition may be based on the desired pH of the final skin treatment composition and/or product. For example, the skin treatment composition may have an amount of pH adjusters such that the pH of the composition is about 3 to about 7, preferably about 3.5 to about 6.5, preferably about 3.5 to about 6, or preferably about 3.5 to about 5.5.

The amount of the pH adjuster in the skin treatment composition may be based on the desired pH of the final skin treatment composition and/or product. For example, the total amount of the pH adjuster may range from about 0.05 to about 20 wt. %, based on the total weight of the skin treatment composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the skin treatment composition.

Chelatinq Agent(s)

The skin treatment composition may, optionally, include chelating agents. The amount of chelating agent present in the skin treatment composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the skin treatment composition.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate. In at least one instance, the chelating agent is trisodium ethylenediamine disuccinate.

Preservative(s)

Preservatives may be included in the skin treatment composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the skin treatment composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Water

The skin treatment composition may include 10 wt. % or more of water. For example, the amount of water present in the skin treatment composition may be about 10 wt. % or more, about 15 wt. % or more, about 20 wt. % or more, about 25 wt. % or more, about 30 wt. % or more, about 35 wt. % or more, about 40 wt. % or more, 45 wt. % or more, 50 wt. % or more, about 55 wt. % or more, about 60 wt. % or more, about 65 wt. % or more, about 70 wt. % or more, about 75 wt. % or more, about 80 wt. % or more, about 85 wt. % or more, or about 90 wt. % or more, based on the total weight of the skin treatment composition. Additionally or alternatively, the skin treatment compositions may have about 95 wt. % or less, about 90 wt. % or less, about 85 wt. % or less, about 80 wt. % or less, about 75 wt. % or less, about 70 wt. % or less, about 65 wt. % or less, about 60 wt. % or less, about 55 wt. % or less, about 50 wt. % or less, about 45 wt. % or less, about 40 wt. % or less, about 35 wt. % or less, about 30 wt. % or less, about 25 wt. % or less, about 20 wt. % or less, about 15 wt. % or less, about 10 wt. % or less, about 5 wt. % or less, about 3 wt. % or less, about 2 wt. % or less, or about 1 wt. % or less, based on the total weight of the skin treatment composition. In some embodiments, the skin treatment compositions have an amount of water based on the above lower and upper limits, such as, e.g., about 40 to about 90 wt. %, about 45 to about 80 wt. %, about 48 to about 75 wt. %, including ranges and subranges therebetween, based on the total weight of the skin treatment composition. Although the skin treatment compositions may be aqueous, in certain embodiments, the skin treatment compositions are free of water (anhydrous) or substantially free of water (substantially anhydrous).

In some embodiments, the skin tightening composition may be devoid of mono-alcohol. Those of skill in the art will appreciate that mono-alcohol may be present in a composition via its presence in one or more of the ingredients; thus, in some embodiments the skin treatment composition may be substantially free of alcohol. For example, alcohol may be present in the skin treatment composition at a concentration that does not exceed 5 wt. %, and in some instances is present not more than 3 wt. %, and in some instances is present not more than 1 wt. %, based on the total weight of the skin treatment composition.

The skin treatment composition may, optionally, include about 10 wt. % or less of miscellaneous ingredients, based on the total weight of the skin treatment composition. Non-limiting examples of miscellaneous ingredients include active ingredients, pH adjusters, preservatives, salts, chelating agent, colorants, salts, antimicrobial agents, fragrances, vitamins, pearlescent agents, odor absorbers, coloring materials, essential oils, fruit extracts, and combinations thereof. One or more of the foregoing miscellaneous ingredients may be excluded from embodiments of the disclosure. The amount of miscellaneous ingredients may be about 10 wt. % or less, about 9 wt. % or less, about 8 wt. % or less, about 7 wt. % or less, about 6 wt. % or less, about 5 wt. % or less, about 4 wt. % or less, about 3 wt. % or less, about 2 wt. % or less, or about 1 wt. % or less, based on the total weight of the skin treatment composition.

EMBODIMENTS OF THE DISCLOSURE

In accordance with an embodiment of the disclosure, provided is a method for improving skin comprising:
reducing the synthesis of melanin by applying a skin treatment composition to skin, the skin treatment comprising:
(i) about 0.1 to about 25 wt. %, preferably about 0.1 to about 16 wt. %, more preferably about 0.1 to about 10 wt. % of acetyl trifluoromethylphenyl valylglycine;
(ii) optionally, about 0.1 to about 90 wt. %, preferably about 0.5 to about 25 wt. %, more preferably about 15 to about 25 wt. %, of a silicone, fatty compound, or a mixtures thereof, wherein the silicone, fatty compound or a mixture thereof comprises a silicone chosen from lauryl peg-9 polydimethylsiloxyethyl dimethicone, dimethylsiloxane, poly dimethylsiloxane, polydimethylsiloxane, dimethicone, acrylate/dimethicone polymer, and mixtures thereof and/or a fatty compound chosen from a fatty alcohol, a fatty ester, a fatty ether, a fatty acid, a hydrocarbon oil, derivatives thereof, and mixtures thereof; and
(iii) optionally, about 0.5 to about 30 wt. %, preferably about 0.5 to about 25 wt. %, more preferably about 5 to about 20 wt. %, of a polyol, wherein the polyol is chosen from ethylene glycol, propylene glycol, butylene glycol, hexylene glycol, pentylene glycol, diethylene glycol, dipropylene glycol, 1,3 propanediol, glycerin, polyethylene glycols, and mixtures thereof;
wherein all weight percentages are based on the total weight of the skin treatment composition.

According with a further embodiment of the disclosure, provided is a method for improving skin comprising:
reducing the synthesis of melanin by applying a skin treatment composition to skin, the skin treatment comprising:
(i) about 0.1 to about 25 wt. %, preferably about 0.1 to about 16 wt. %, more preferably about 0.1 to about 10 wt. % of acetyl trifluoromethylphenyl valylglycine; wherein all weight percentages are based on the total weight of the skin treatment composition.

In accordance with another embodiment, provided is a method for treating skin having one or more of eczema, acne, and psoriasis, the method comprising:
reducing inflammation of the skin having one or more of eczema, acne, and psoriasis by applying an amount of skin treatment composition, the skin treatment composition comprising:
(i) about 0.1 to about 25 wt. %, preferably about 0.1 to about 16 wt. %, more preferably about 0.1 to about 10 wt. % of acetyl trifluoromethylphenyl valylglycine;
(ii) optionally, about 0.1 to about 90 wt. %, preferably about 0.5 to about 25 wt. %, more preferably about 15 to about 25 wt. %, of a silicone, fatty compound, or a mixtures thereof, wherein the silicone, fatty compound or a mixture thereof comprises a silicone chosen from lauryl peg-9 polydimethylsiloxyethyl dimethicone, dimethylsiloxane, poly dimethylsiloxane, polydimethylsiloxane, dimethicone, acrylate/dimethicone polymer, and mixtures thereof and/or a fatty compound chosen from a fatty alcohol, a fatty ester, a fatty ether, a fatty acid, a hydrocarbon oil, derivatives thereof, and mixtures thereof; and
(iii) optionally, about 0.5 to about 30 wt. %, preferably about 0.5 to about 25 wt. %, more preferably about 5 to about 20 wt. %, of a polyol, wherein the polyol is chosen from ethylene glycol, propylene glycol, butylene glycol, hexylene glycol, pentylene glycol, diethylene glycol, dipropylene glycol, 1,3 propanediol, glycerin, polyethylene glycols, and mixtures thereof,
wherein all weight percentages are based on the total weight of the skin treatment composition.

According to another embodiment, provided is a method for treating skin suffering from one or more of eczema, acne, and psoriasis, the method comprising:
reducing inflammation of the skin having one or more of eczema, acne, and psoriasis by applying an amount of skin treatment composition, the skin treatment composition comprising:
(i) about 0.1 to about 25 wt. %, preferably about 0.1 to about 16 wt. %, more preferably about 0.1 to about 10 wt. % of acetyl trifluoromethylphenyl valylglycine, wherein all weight percentages are based on the total weight of the skin treatment composition.

In accordance with yet a further embodiment, provided is a skin treatment composition that typically includes:
about 0.1 to about 25 wt. %, preferably about 0.1 to about 16 wt. %, more preferably about 0.1 to about 10 wt. % of acetyl trifluoromethylphenyl valylglycine;
about 0.1 to about 30 wt. %, preferably about 0.5 to about 25 wt. %, more preferably about 15 to about 25 wt. %, of a silicone, fatty compound, or a mixtures thereof, wherein the silicone, fatty compound or a mixture thereof comprises a silicone chosen from lauryl peg-9 polydimethylsiloxyethyl dimethicone, dimethylsiloxane, poly dimethylsiloxane, polydimethylsiloxane, dimethicone, acrylate/dimethicone polymer, and mixtures thereof and/or a fatty compound chosen from a fatty alcohol, a fatty ester, a fatty ether, a fatty acid, a hydrocarbon oil, derivatives thereof, and mixtures thereof;
optionally, about 0.5 to about 30 wt. %, preferably about 0.5 to about 25 wt. %, more preferably about 5 to about 20 wt. %, of a polyol, wherein the polyol is chosen from ethylene glycol, propylene glycol, butylene glycol, hexylene glycol, pentylene glycol, diethylene glycol, dipropylene glycol, 1,3 propanediol, glycerin, polyethylene glycols, and mixtures thereof, wherein all weight percentages are based on the total weight of the skin treatment composition; and
optionally, greater than zero to about 10 wt. %, preferably about 10 ppm to about 10 wt. %, more preferably about 0.1 to about 10 wt. %, of a skin active agent chosen from sodium hyaluronate, capryloyl salicylic acid, coco-caprylate/caprate, alpha and/or beta arbutin, ferulic acid, lucinol, kojic acid, resorcinol, tranexamic acid, gentisic acid, homogentisic, methyl gentisate or homogentisate, dioic acid, D pantheteine calcium sulphonate, lipoic acid, ellagic acid, vitamin B3, linoleic acid, stilbenoid, coumarin, tannin, curcuminoid, chalcone, phenylpropanoid, anthocyanin, dihydrochalcone, anthocyanidin, tocopherols, sesame lignin, vitamin C, derivatives thereof, salts thereof, and mixtures thereof.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The examples serve to illustrate the technology without being limiting in nature.

Example 1

(Example Compositions)

| Example Composition 1 (Ex. 1) | | |
| --- | --- | --- |
| | US INCI ingredient names | Wt. % |
| Acetyl trifluoro-methylphenyl valylglycine | ACETYL TRIFLUOROMETHYLPHENYL VALYLGLYCINE | 10 |
| Silicone | CETYL PEG/PPG-10/1 DIMETHICONE, PEG/PPG-18/18 DIMETHICONE, DIMETHICONE, C30-45 ALKYL DIMETHICONE, and DIMETHICONOL | 15 |
| Emollient | PENTAERYTHRITYL TETRAETHYLHEXANOATE | 2 |
| Fatty compound | ETHYLHEXYL PALMITATE and ISOHEXADECANE | 5 |
| Polyol | GLYCERIN, CAPRYLYL GLYCOL, and BUTYLENE GLYCOL | 8 |
| Skin Active Agents | CENTELLA ASIATICA EXTRACT, SODIUM PALMITOYL PROLINE, NYMPHAEA ALBA FLOWER EXTRACT, and SODIUM CARBOXYMETHYL BETA-GLUCAN | 1 |
| Miscellaneous (preservatives, bulking agent, pH adjusters, and/or the like) | PHENOXYETHANOL, SODIUM BENZOATE, MAGNESIUM SULFATE, and CITRIC ACID | 1 |
| Water | DEIONIZED WATER | QS to 100 |

Example 2

(Evaluation of Prostaglandin $E_2$ and Acetyl Trifluoromethylphenyl Valylglycine)

Six cultures of human primary melanocytes were grown for four days. Thereafter, the cultures were treated with 10 μL of one of Compositions A-E each day for ten days. Composition A contained 0.005 wt. % of acetyl trifluoromethylphenyl valylglycine, 2 wt. % ethanol, and the remainder being water. Composition B contained 0.05 wt. % of acetyl trifluoromethylphenyl valylglycine, 2 wt. % ethanol, and the remainder being water. Composition C contained 30 nM of prostaglandin $E_2$, 2 wt. % ethanol, and the remainder being water. Composition D contained 0.005 wt. % of acetyl trifluoromethylphenyl valylglycine, 30 nM of prostaglandin $E_2$, 2 wt. % ethanol, and the remainder being water. Composition E contained 0.05 wt. % of acetyl trifluoromethylphenyl valylglycine, 30 nM of prostaglandin $E_2$, 2 wt. % ethanol, and the remainder being water. All weight percentages for Compositions A-E were based on the total weight of the respective composition. The media for the cultures was changed each day over the ten-day period.

Figure 2:
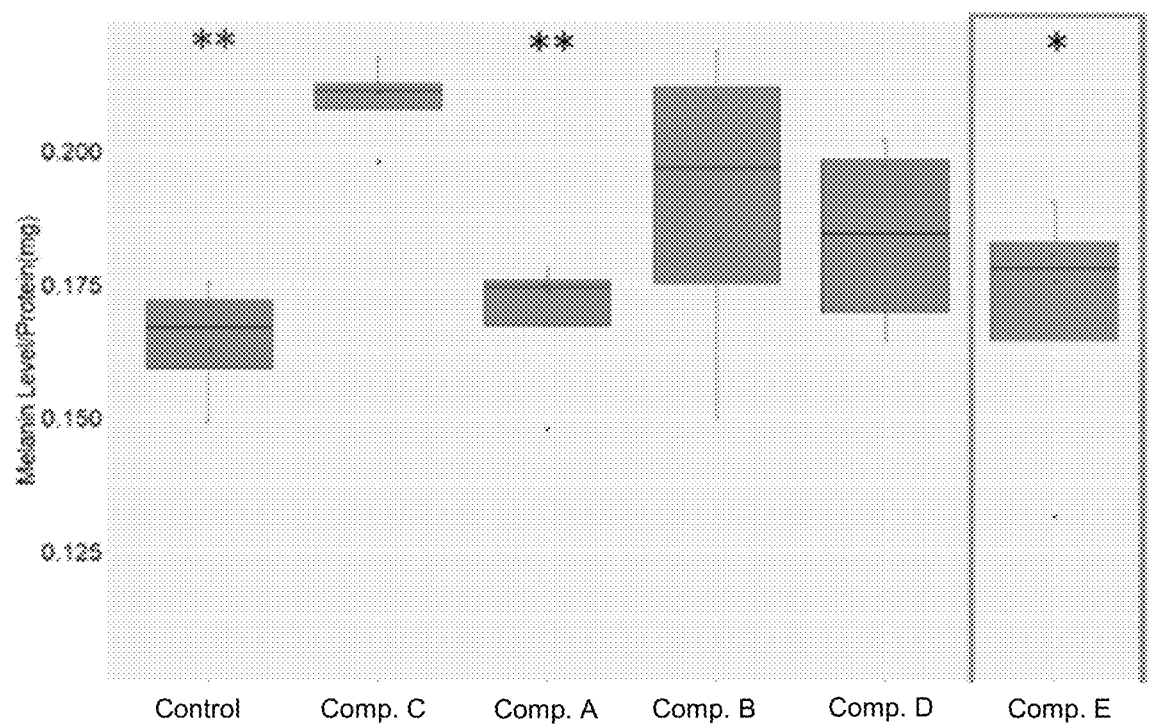
FIG. 2 is a bar graph showing the amount of melanin in the in vitro skin cells of FIG. 1.

After the 10 days, the cells of the culture were lysed and the melanin content was measured. Specifically, the cells were stained with Fontana Masion Staining and measured with a plate reader. A BCA assay was performed to quantify the protein concentration. The cells were also imaged using a fluorescent microscope at 10× magnification (Leica DMI8, Leica). To eliminate the melanin content caused by increased NHEM cell number in the system, the final melanin level was calculated by dividing the protein content in each culture. FIG. 1 is images of the cells after lysing and staining of the melanin. FIG. 2 is a bar graph showing the amount of melanin in the six groups of cells after the ten days of treatment.

As seen in FIGS. 1 and 2, prostaglandin $E_2$ stimulates melanin production, and acetyl trifluoromethylphenyl valylglycine reduces melanin synthesis after induction by prostaglandin $E_2$. Notably, the cells that received Composition E—0.05 wt. % of acetyl trifluoromethylphenyl valylglycine and 30 nM of prostaglandin $E_2$—exhibited an amount of melanin synthesis that was similar to the control. Without being limited to any specific theory, it is believed that the compositions in accordance with aspects of the disclosure provide an improvement to skin tone, such as reducing dyschromia, by reducing the synthesis of melanin.

Example 3

Evaluation of Acetyl Trifluoromethylphenyl Valylglycine on Post Inflammatory Hyperpigmentation The efficacy of acetyl trifluoromethylphenyl valylglycine to modulate key gene markers in the inflammatory pathway as it relates to post inflammatory hyperpigmentation conditions was evaluated. Specifically, four well plates were seeded with a single cell culture of normal human epidermal melanocyte (NHEM), and grown in a culture medium (namely, culture medium no. M254500, obtained from ThermoFisher™) and supplemented with Gibco™ human melanocyte growth supplement (namely, Human Melanocyte Growth Supplement-2 no. S0165, obtained from ThermoFisher™) at a density of 10,000 cells/cm² for 3 to 4 days.

The culture medium was then replaced by culture mediums containing different treatments. Specifically, the cell cultures were treated with 10 μL of one of Compositions C-E once a day for ten days (except weekends). After 10 days, the cells were trypsinized and centrifuged at 180×gravity for 7 minutes followed by RNA isolation using a QIAshredder cell lysate homogenizer no. 79654, which was available from Qiagen™. RNA was isolated according to manufacturer's instructions. The RNA was then quantified using the NanoDrop Spectrophotometer.

After RNA isolation was completed, samples of 1 μg of RNA from each cell culture was used for cDNA reactions for reverse transcription. Parameters for the reverse transcription were as follows: a temperature of 25° C. for 10 minutes, a temperature of 37° C. for 2 hours, and then a temperature of 85° C. for 5 minutes. For qRT-PCR reverse transcription, a sample of 10 ng of cDNA was used per reaction. The gene expression of COX-2 and p38 gene expression were normalized against to TATA-binding protein (TBP, housekeeping gene). The ΔCt values were generated for the target genes by using the housekeeping Ct value for each respective biological replicate. The ΔCt values were averaged and used to calculate the ΔΔCt values. The ΔΔCt values were then determined for each biological replicate by normalizing to the appropriate untreated control average ΔCt value. The ΔΔCt values were then used to calculate relative quantification (RQ) values.

Figure 3A:
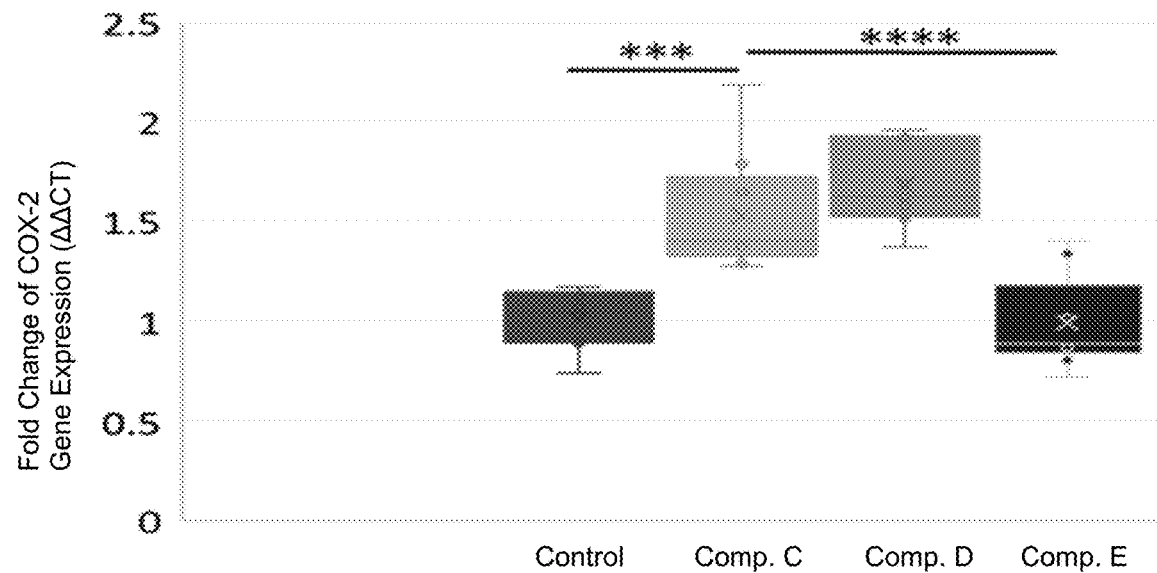
FIGS. 3A and 3B are bar graphs showing the amount of COX-2 expression and p38 gene expression, respectively, for cell cultures treated with compositions containing prostaglandin $E_2$, acetyl trifluoromethylphenyl valylglycine, and combinations thereof in accordance with aspects of the disclosure.
Figure 3B:
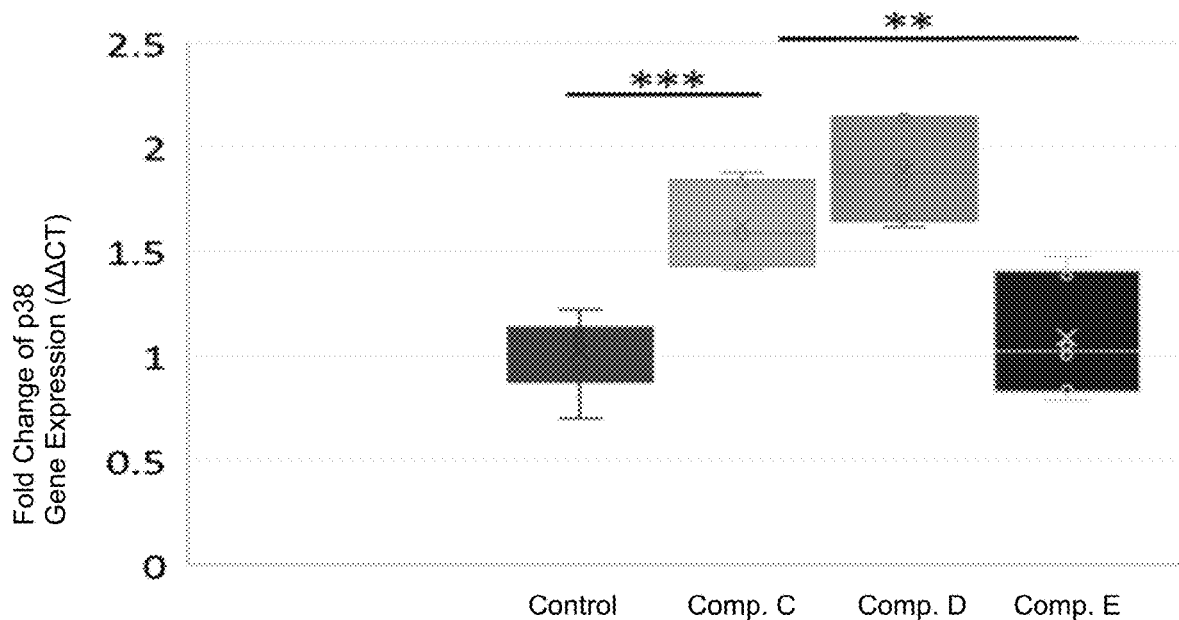

As seen in FIGS. 3A and 3B, prostaglandin $E_2$ triggered the cascade of cyclooxygenase-2 (COX-2) and p38 mitogen-activated protein kinase (p38 MAPK) pathway in NHEM, while acetyl trifluoromethylphenyl valylglycine significantly attenuated the level of COX-2 and P38 MAPK induced by prostaglandin $E_2$. Prostaglandin $E_2$ is an endogenous lipid mediator of inflammation, which is typically upregulated in post-inflammatory hyperpigmentation (PIH) related skin disorders. Without being limited to any specifically theory, it is believed that the two major processes that result in PIH are overproduction of melanin and an irregular dispersion of pigment after cutaneous inflammation. The determination that acetyl trifluoromethylphenyl valylglycine modulates COX-2 and P38 MAPK (two of the key signaling genes in inflammatory pathway) suggests that the skin treatment compositions disclosed herein would be effective for modulating inflammation and pigmentation as driven by post-inflammatory hyperpigmentation (PIH) conditions.

Example 4

(Evaluation of Exemplary Composition 1's Effect on Dyschromia)

The benefits of applying Exemplary Composition 1 after a procedure that reduces the barrier function of skin was evaluated. Specifically, thirty-three female volunteers having skin exhibiting mild to severe crow's feet wrinkles (2-5.6/0-6 Atlas Scale); mild to severe dyschromia (3.5-8/0-9 Griffith Scale); and mild to severe roughness (3.5-8/0-9 Griffith Scale) completed this evaluation.

After the volunteers received a non-ablative fractional laser resurfacing procedure, each volunteer received 5 mg of Example Composition 1 on a first half of their face and received 5 mg of Comparative Composition F on the second half of their face. The application of Example Composition 1 and Comparative Composition F occurred once in the morning and once in the afternoon or evening for 28 days. The list of ingredients for Comparative Composition F is provided below.

Petrolatum, mineral oil, ceresin, lanolin alcohol, panthenol, glycerin, and bisabolol.

Figure 4:
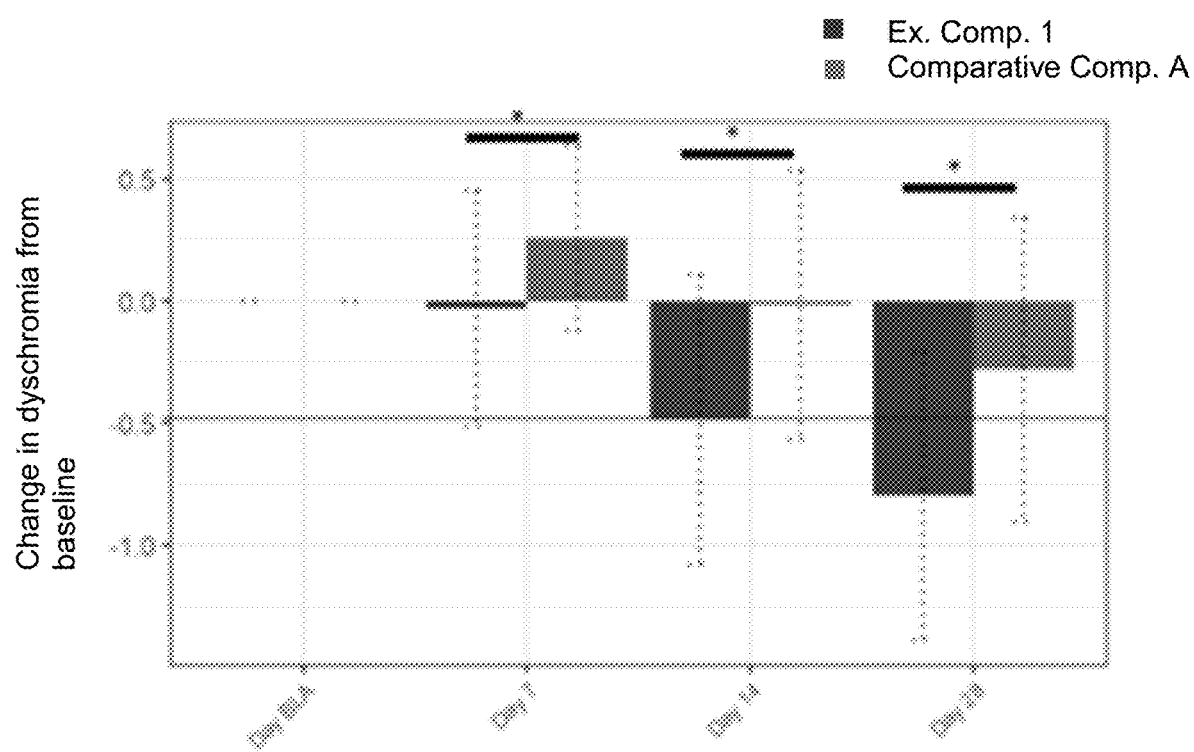
FIG. 4 is a bar graph evaluating the change in dyschromia after receiving an application of a non-limiting exemplary skin treatment composition or a comparative composition according to aspects of the disclosure.

The volunteers were then evaluated to assess dyschromia. The results of the change in dyschromia are presented as a bar graph in FIG. 4. Exemplary Composition 1 provided a significantly better reduction in dyschromia at day 7, day 14, and day 28. Specifically, Exemplary Composition 1 provided significantly reduce skin dyschromia by day 14 and day 28 with clinical significance, and significantly outperform the clinical benchmark of Comparative Composition F. Additionally, Exemplary Composition 1 prevented the increase in inflammation caused by the non-ablative fractional laser resurfacing procedure on day 7. Notably, Comparative Composition F did not prevent the inflammation on day 7, which was caused by the non-ablative fractional laser resurfacing procedure.

Example 5

(Skin Layer Evaluation of Acetyl Trifluoromethylphenyl Valylglycine)

Tri-culture models, co-culture models, and single cell culture models were treated with a composition containing acetyl trifluoromethylphenyl valylglycine to assess the effects on different skin cells. Specifically, the three cultures for each of the tri-culture models (Normal Human Epidermal Melanocytes, Normal Human Epidermal Keratinocytes, and Normal Human Dermal Fibroblast), co-culture models (Normal Human Epidermal Melanocytes and Normal Human Epidermal Keratinocytes), and single cell culture models (Normal Human Epidermal Melanocytes) were grown for four days. The cultures were then treated once a day for 10 days with a composition containing 10% DMSO, water, and lipoic acid (Composition G) in an amount to deposit 25 μm to the cell culture models, a composition containing 10% DMSO, water, and acetyl trifluoromethylphenyl valylglycine (Composition H) in an amount to deposit 100 μm to the cell culture models, or a composition containing 10% DMSO, water, and acetyl trifluoromethylphenyl valylglycine (Composition I) in an amount to deposit 300 μm to the cell culture models. The media for the cultures was changed each day over the ten-day period.

Figure 5:
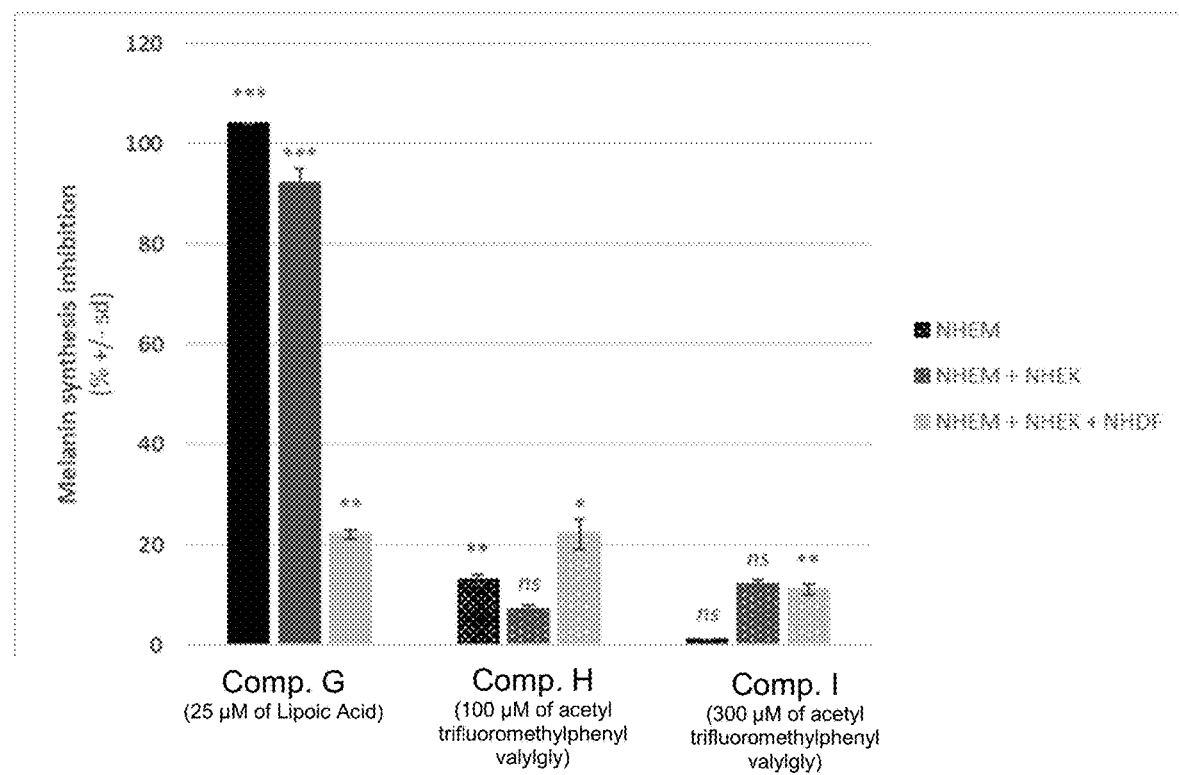
FIG. 5 is a bar graph illustrating the level of melanin synthesis inhibition for the cell cultures based on the treatment of the compositions containing lipoic acid or acetyl trifluoromethylphenyl valylglycine in accordance with aspects of the disclosure.

After the 10 days, the cells of the culture were lysed and the melanin content was measured using a procedure and equipment similar to that described in Example 2. FIG. 5 is a graph illustrating the level of melanin synthesis inhibition for the cell cultures based on the treatment of the compositions containing lipoic acid or acetyl trifluoromethylphenyl valylglycine.

As seen in FIG. 5, 100 μM of acetyl trifluoromethylphenyl valylglycine inhibited L-Tyrosine-induced melanin synthesis in tri-culture model (K/M/F). Interestingly, while the amount of acetyl trifluoromethylphenyl valylglycine did not appear to inhibit melanin synthesis in the co-culture on melanocytes and keratinocytes, an inhibitory effect was observed for the melanocytes cultures. The inhibitory effect for the melanocytes cultures was less than the observed in the tri-culture. Without being limited to any particular theory, it is believed that the inhibition of melanin synthesis in a tri-culture model (K/M/F) by acetyl trifluoromethylphenyl valylglycine inhibits is at least partially due to the presence of fibroblasts.

The invention claimed is:

1. A method for managing skin tone in skin in need thereof, comprising:
    (a) subjecting the skin to a procedure that induces melanin synthesis, the procedure selected from a laser procedure, a microneedle procedure, a cryotherapy procedure, a radiofrequency microneedle procedure, or combinations thereof, and inducing the melanin synthesis;
    (b) applying to the skin that has been subjected to the procedure an effective amount of a skin treatment composition comprising:
        (i) about 0.1 to about 25 wt. % of acetyl trifluoromethylphenyl valylglycine;
        (ii) about 0.1 to about 90 wt. % of a silicone, a fatty compound, or a mixture thereof; and
        (iii) water;
            wherein all weight percentages are based on a total weight of the skin treatment composition; and
    (c) reducing the synthesis of melanin induced by the procedure.

2. The method of claim 1, wherein the method reduces the synthesis of melanin by about 5% or more.

3. The method of claim 1, wherein the method reduces the synthesis of melanin by about 15% or more.

4. The method of claim 1, wherein the skin treatment composition is applied at least twice a day after subjecting the skin to the procedure.

5. The method of claim 1, wherein the skin treatment composition is applied at least once a day for about 20 or more days after subjecting the skin to the procedure.

6. The method of claim 1, wherein the acetyl trifluoromethylphenyl valylglycine is applied to the skin in an amount of about 0.1 to about 9 g/dm$^2$.

7. The method of claim 1, wherein the skin treatment composition further comprises:
    (iv) about 0.5 to about 30 wt. % of one or more polyols selected from ethylene glycol, propylene glycol, butylene glycol, hexylene glycol, pentylene glycol, diethylene glycol, dipropylene glycol, 1,3-propanediol, glycerin, polyethylene glycols, or mixtures thereof.

8. The method of claim 6, wherein the skin treatment composition further comprises:
    (v) about 0.1 to about 30 wt. % of one or more fatty compounds selected from fatty alcohols, fatty esters, fatty ethers, fatty acids, plant based oil, hydrocarbon oils, or mixtures thereof.

9. The method of claim 8 comprising one or more fatty alcohols selected from decyl alcohol, undecyl alcohol, dodecyl alcohol, myristyl alcohol, lauryl alcohol, cetyl alcohol, stearyl alcohol, cetearyl alcohol, isostearyl alcohol, isocetyl alcohol, behenyl alcohol, linalool, oleyl alcohol, isotridecyl alcohol, arachidyl alcohol, or mixtures thereof.

10. The method of claim 8 comprising one or more plant based oils selected from coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazelnut oil, grapeseed oil, colza oil, cade oil, peach kernel oil, coffee bean oil, jojoba oil, or mixtures thereof.

11. The method of claim 1, wherein the skin treatment composition is an emulsion.

12. The method of claim 1, wherein the skin is skin under the eye.

13. The method of claim 1, wherein the skin treatment composition is not a gel.

14. The method of claim 13, wherein the skin treatment composition is free from celluloses.

15. The method of claim 1, wherein the skin treatment composition is free from celluloses.

16. A method for managing skin tone in skin in need thereof, comprising:
    (a) subjecting the skin to a procedure that induces melanin synthesis, the procedure selected from a laser procedure, a microneedle procedure, a cryotherapy procedure, a radiofrequency microneedle procedure, or combinations thereof, and inducing the melanin synthesis;
    (b) applying to the skin that has been subjected to the procedure an effective amount of a skin treatment composition comprising:
        (i) about 0.1 to about 25 wt. % of acetyl trifluoromethylphenyl valylglycine;
        (ii) about 0.1 to about 90 wt. % of a silicone, a fatty compound, or a mixture thereof;
        (iii) water;
        (iv) about 0.5 to about 30 wt. % of one or more polyols selected from ethylene glycol, propylene glycol, butylene glycol, hexylene glycol, pentylene glycol, diethylene glycol, dipropylene glycol, 1,3-propanediol, glycerin, polyethylene glycols, or mixtures thereof; and
        (v) about 0.1 to about 30 wt. % of one or more fatty compounds selected from fatty alcohols, fatty esters, fatty ethers, fatty acids, plant based oil, hydrocarbon oils, or mixtures thereof; wherein all weight percentages are based on a total weight of the skin treatment composition; and
    (c) reducing the synthesis of melanin induced by the procedure.

17. The method of claim 16, wherein the method reduces the synthesis of melanin by about 5% or more.

18. The method of claim 16, wherein the method reduces the synthesis of melanin by about 15% or more.

* * * * *